United States Patent [19]
Konig et al.

[11] 4,441,616
[45] Apr. 10, 1984

[54] PROCESS FOR SORTING COARSE TO FINE MATERIALS ACCORDING TO THEIR CHEMICAL COMPOSITION

[75] Inventors: Rainer Konig, Eshborn; Hans-Ulrich Freund, Friedrichsdorf; Helga Heide, Kelkheim; Rolf A. Sieglen, Sulzbach, all of Fed. Rep. of Germany

[73] Assignee: International Business Machines Corporation, Armonk, N.Y.

[21] Appl. No.: 212,728

[22] PCT Filed: Feb. 22, 1980

[86] PCT No.: PCT/EP80/00010
§ 371 Date: Oct. 27, 1980
§ 102(e) Date: Oct. 27, 1980

[87] PCT Pub. No.: WO80/01837
PCT Pub. Date: Sep. 4, 1980

[30] Foreign Application Priority Data
Feb. 26, 1979 [DE] Fed. Rep. of Germany ....... 2907513

[51] Int. Cl.³ .......................... B07C 5/00; E21C 41/06
[52] U.S. Cl. ..................................... 209/44.1; 299/10; 299/18; 436/26; 436/177
[58] Field of Search .......................... 209/1–3, 209/3.1, 44.1; 73/28; 299/1, 7, 10, 18; 436/2, 26, 28, 174, 177, 181, 183

[56] References Cited

U.S. PATENT DOCUMENTS

| | | | |
|---|---|---|---|
| 3,743,356 | 7/1973 | Sheets | 299/18 |
| 3,843,198 | 10/1974 | Reynolds | 299/18 |
| 3,868,222 | 2/1975 | Barringer | 73/28 X |
| 4,152,923 | 5/1979 | Courbon | 73/28 |
| 4,249,655 | 2/1981 | Patureau et al. | 209/3 X |

FOREIGN PATENT DOCUMENTS

| | | |
|---|---|---|
| 2042227 | 3/1972 | Fed. Rep. of Germany . |
| 1554504 | 2/1968 | France . |
| 2271880 | 5/1974 | France . |

*Primary Examiner*—Randolph Reese
*Assistant Examiner*—Edward M. Wacyra
*Attorney, Agent, or Firm*—Joscelyn G. Cockburn; Earl C. Hancock

[57] ABSTRACT

Process for sorting coarse to fine materials according to their chemical composition, in which samples are taken and analyzed, and in which the transporting and/or further processing of the materials is controlled according to the results of the analysis. The samples are taken in the form of an air swirled mixture of coarse dust and fine dust (i.e., particles with grain sizes of less than 200 μm) which is obtained as a by-product or is produced artificially. The coarser dust is separated from the mixture. All of the fine dust or a fraction thereof is analyzed.

24 Claims, 8 Drawing Figures

U.S. Patent  Apr. 10, 1984  Sheet 1 of 3  4,441,616
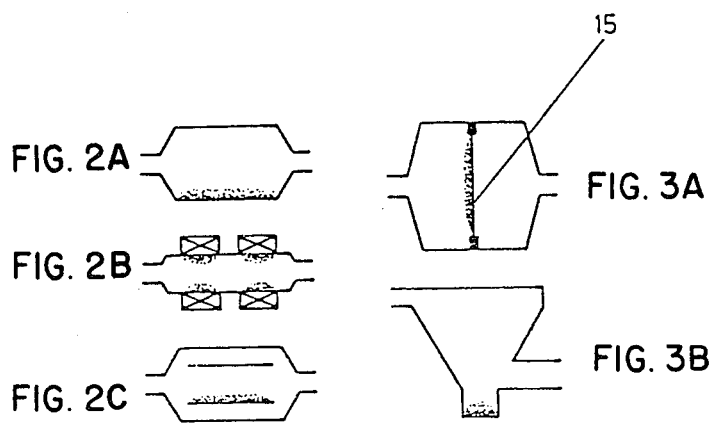
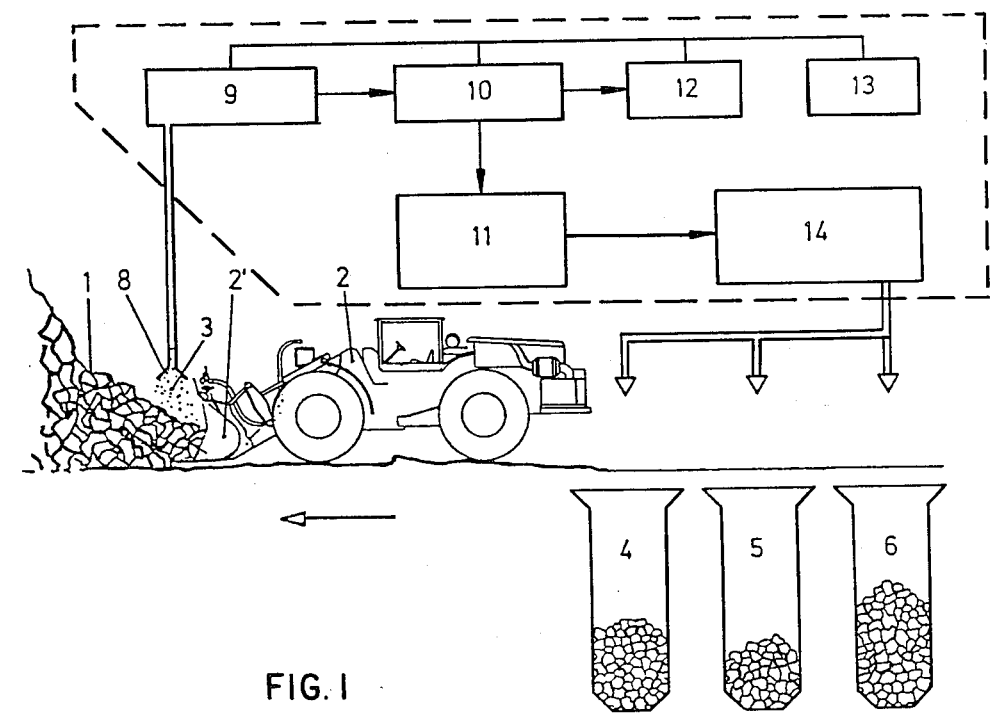
FIG. 1

PROCESS FOR SORTING COARSE TO FINE MATERIALS ACCORDING TO THEIR CHEMICAL COMPOSITION

BACKGROUND OF THIS INVENTION

1. Field of this Invention

This invention relates to a process for sorting coarse to fine materials according to their chemical composition, in which samples are taken and analyzed, and in which the transporting and/or further processing of the materials is controlled according to the results of the analysis.

2. Prior Art

When mining mineral raw materials, it is necessary for an economical process that the composition of the raw material be constantly controlled. On the one hand this determines the proportion of waste rock or pay gravel, and on the other it is often necessary to keep certain disturbing admixtures under control. For these measurements, a sample must be obtained for analysis which is as representative as possible of the batch of raw material under consideration. Normally, random samples of the raw material are taken using a shovel or some other grabbing tool. The sample is then prepared for the actual chemical analysis (ground homogenized). This presents two important problems, namely:

obtaining a really representative sample; and conducting the analysis in such a short time that, depending on the result of the analysis, it is possible to intervene in the transporting or further processing of the materials.

Since the total analysis (taking the sample, preparation and chemical analysis) takes a relatively long time (at least ten minutes), it has so far only been possible to take samples and intervene in the process according to the results of the analysis at intervals which are too great. The result of this in mining iron ore in a large underground mine, for example, is the undesired mixing of ores having different phosphorus contents. This mixing of ores causes the yield of low-phosphorous ore to fall far below what is possible from a geological point of view. The mixing occurs directly at the mining site. The blasted ore is transported to shafts approximately 40 to 200 m away using power shovels (one shovel holds about 8 tons). A sample weighing around 1 kilogram is taken only from about every tenth shovel using a grabbing tool. This sample is ground, sifted and magnetically separated, with one part of it then being dried; and a part thereof is measured and analyzed by wet chemical methods. On the basis of the results of this analysis, all further shovels are tipped into the shaft provided for the grade analyzed until the results of the next analysis are available, although the composition of the material generally changes from one shovel to the next. The phosphorus content, which is an important determinant of quality, may vary by a factor between 10 and 100.

BROAD DESCRIPTION OF THIS INVENTION

The object of this invention is to develop a process by which representative samples of the material, which is to be analyzed and passed on in sorted form, can be taken and analyzed within a sufficiently short time. By this process, a sample is taken from each shovel when mining ore as described above, and is analyzed so quickly that the contents of the shovel can be transported without delay to the shaft provided for this ore composition or for this quality. This permits a much more precise sorting of the material mined. (Fine dust: particles having grain sizes of less than 200 $\mu$m, and in particular cases, e.g., iron ore, less than 100 $\mu$m.)

It has now been shown that this object can be achieved in a technically advanced manner, in the known process as described above, if the samples are taken in the form of a raised mixture of coarse and fine dust, which is obtained as a by-product or is produced artificially, if the coarse dust is then separated, and if the remaining fine dust or a fraction of this fine dust is analyzed. The process of this invention can be used in the mining or processing of minerals, such as, ore, coal, basalt, sand, etc., or semi-finished products, such as, minerals in the form of pellets, coke, and many other materials.

The dust sample can be precipitated on a filter or collected in a small jar. The amount of dust yielded will generally be in the order of 10 to 100 mg. X-ray fluorescence analysis, for example, can be used as a method of analysis for the filter samples. Whenever the substance of the sample is precipitated in a jar, the analysis can be made by way of an adapted wet-chemical process. In the case of an iron ore sample (magnetic and apatite) for example, the apatite which contains the phosphorus determining the quality, can be dissolved by hot reagents and analyzed.

Other elements can be analyzed using particular physical properties, for example, using the ferromagnetism of the magnetite.

Another suitable method for the rapid analysis of the dust sample is plasma emission spectroscopy. In this case the dust can be either blown directly into the plasma or evaporated before injection. Due to the small grain size of the dust, vaporization occurs instantaneously.

Using the results of the analysis which are available within a very short time after the beginning of the sampling (about 1 min.), it is possible to decide on the further course of the batch of raw mineral analyzed while it is still being transported. Batches outside of the predetermined quality standards can be rejected or mixed with correspondingly good batches in order to obtain a uniform quality of raw material. At the same time undesired mixing, which cannot be reversed later, can be avoided. Other advantages of analyzing the materials, for example, mineral raw materials, within the scope of the process according to this invention using the collected mixture of coarse and fine dust, which is produced artificially or obtained during processing, are that:

the sample obtained is directly suitable for rapid chemical analysis without grinding or other preparation;

the representativeness of the samples is easily achieved by process engineering; an the representativeness of the sample is, in the case of strongly nonhomogeneous material composition, superior to the conventionally obtained samples.

These advantages together lead to a considerably more rapid analysis of the materials as compared to the known and conventional process customarily used today.

It is also important that the process according to the invention may be carried out with relatively simple equipment which requires little servicing.

According to a favorable embodiment of the process according to this invention, the dust mixture is produced during sampling by compressed air in such a way that during the loading process the load of ore is repeatedly blown-at and the raised dust is sucked away.

Moreover, in another embodiment of this invention it is possible to separate the coarser particles from the dust mixture in one or several stages either by gravimetric methods and/or using filters. At the same time, dust particles of specific composition can be removed from the ensuing chemical analysis either by magnetic or electrostatic separation. It has been shown that in many cases a particular grain size fraction is more representative for the chemical composition of the material to be analyzed than the remaining dust fractions. This is due, for example, to the fact that in sampling or in sucking up the coarser dust particles there is a tendency for random selection processes to occur or for fine grained dust from the surroundings to occur simultaneously.

Furthermore, the process according to this invention makes provision for the fine dust to be applied to a diaphragm filter, and then the whole unit, for example, after being encapsulated in a hermetically sealable cassette, is transported for chemical analysis. The transportation of such samples can be accomplished rapidly by a pneumatic conveyor system without contamination by ambient dust.

DETAILED DESCRIPTION OF THIS INVENTION

Other features, advantages and possible applications of this invention can be seen from the following description of other details in the below-described embodiments and from the drawings.

In the drawings (in simplified form):

FIG. 1 is a schematic diagram, etc., showing the principle of a device for conducting the process according to this invention;

FIG. 2A is a cross-sectional side elevational view of one of the embodiments of the primary separator of the device according to FIG. 1;

FIG. 2B is a cross-section side elevational view of another embodiment of the primary separator of the device according to FIG. 1;

FIG. 2C is a cross-sectional side elevational view of a further embodiment of the primary separator of the device according to FIG. 1;

FIG. 3A is a cross-sectional side elevational view of one of the embodiments of the dust collector of the device according to FIG. 1;

FIG. 3B is a cross-sectional side elevational view of another embodiment of the dust collector of the device according to FIG. 1;

Figure 4:
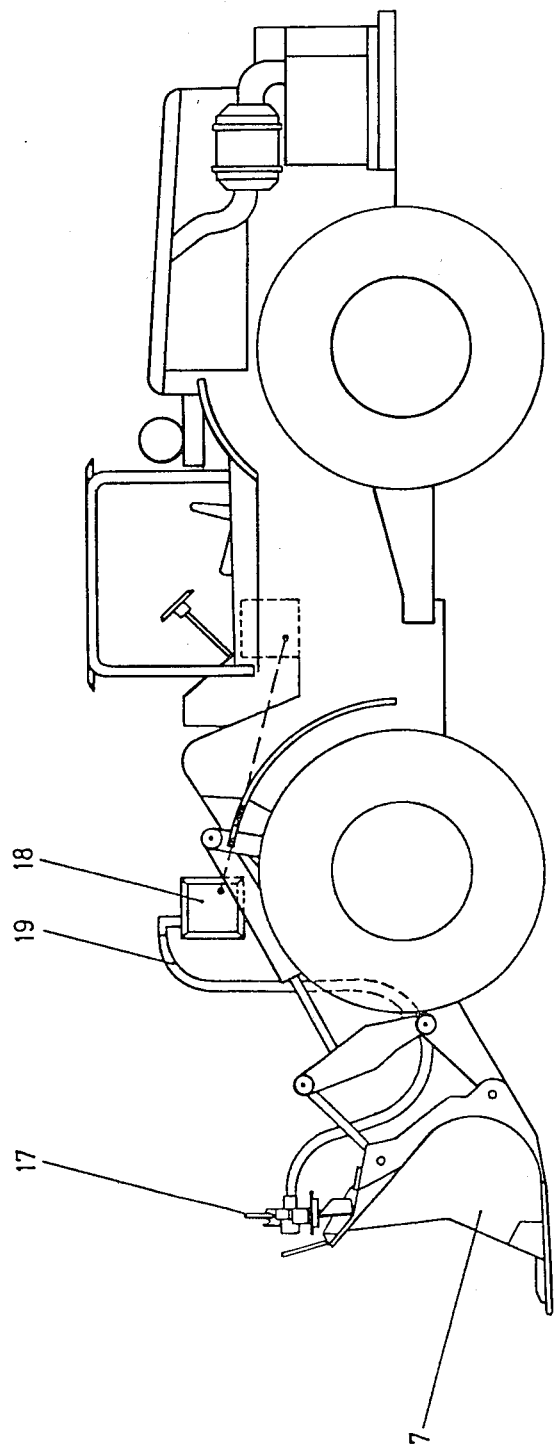
FIG. 4 is a side elevational view of a power shovel with an embodiment of the device according to FIG. 1.

In the example shown in FIG. 1 iron ore 1 is transported to collection shafts 4 to 6 in front end loader 2. In this embodiment, when ore 1 is loaded into shovel 2; developing dust is sucked in with the help of dust collecting head 8. Unit 12 represents a suction pump. If sufficient dust is not available or if the naturally obtained dust is not sufficiently representative, then the required volume of dust is produced by blowing compressed air at ore 1 or by dust collecting devices, etc., disposed near dust collecting head 8. Dust collecting head 8 advantageously contains a pre-filter (not shown in FIG. 1) in order to limit the maximum grain size of the sample even at this point.

Depending on the type of material being examined, dust particles of specific properties are eliminated from further investigation by adjoining separator 9 (see also FIG. 2). The remaining dust is then removed from the air flow using dust separator 10 (see also FIG. 3). The dust carrier—a dust filter or a container, depending on the design of dust separator 10—is then passed on to rapid analyzer 11.

The course of the total process from sampling to rapid analysis (start and end of the suction process, synchronization with a blowing device or with a grinding tool for producing the dust, operation of the separator, air throughput, and transport and removal of the sample) is controlled by control unit 13, shown in diagrammatic form in FIG. 1, and can then be repeated in rapid succession.

The result of the analysis determines the further treatment of mineral 1 in loader 2. In the embodiment diagrammed, the result of the rapid analysis in stage 11 determines the further treatment of mineral 1 in loader 2. The result of the rapid analysis is evaluated in control unit 14, by means of which mineral 1 is transported further to shaft 4, 5 or 6 according to its "grade".

FIGS. 2A to 2C illustrate the various principles on which the dust separation in separator 9 can be based. In FIG. 2A gravimetric separation is used, while in FIG. 2B the particles are separated magnetically and in FIG. 2C the particles are separated electrostatically. In practice one specific method or a combination of several methods will usually be used.

Either a filter separating arrangement (as shown in FIG. 3A) or a cyclone or impactor (as shown in FIG. 3B) can be used as dust separator 10. Filter insert 15 of dust separator 10 (FIG. 3A) is preferably encapsulated in a container and passed on with such container to rapid analysis in stage 11.

FIG. 4 shows shovel loader 7 used in ore mining with a device for carrying out the process according to this invention. Dust collecting head 8, as shown in FIG. 1, is in this case a part of dust collecting unit 17. Unit 17 also incorporates separator 9 and dust separator 10 (see FIG. 1). Turbine 18, which is connected to dust collecting unit 17 by flexible tube 19, serves as suction pump 12. Turbine 18 is designed for an air throughput of from 1 to 3.5 $m^3/h$ related to the cross sectional surface (in $cm^2$) of the diaphragm filter inserted in the diaphragm filter, which is inserted in the collecting device—comparable to filter 15, as in FIG. 3A—or up to about 300 $m^3/h$. Whenever the dust obtained during loading is not sufficient, an increase of the air flow above shovel 7 is secured with the help of compressed air (the devices needed for this are of a traditional nature and have not been shown therefore) so that dust is also transported into collecting device 16 even from areas of shovel 7 lying further away. Collecting device 17 contains a pre-filter followed by a filter unit as in FIG. 3A or an impactor as in FIG. 3B. Because of the great variations in the mean size of the ore chunks of the material to be loaded, the available volume of dust also greatly fluctuates. By the arrangement of the nozzles with the help of compressed air (6 atm.) in this example, and also by the high intake performance of the collecting device, it is ensured that sufficient material of dust samples is collected in all cases. A suction time of about 20 seconds is sufficient to collect an adequate quantity of dust mixture for the analysis (about 30 mg). Subsequently, the dust sample is analyzed within a short time on board the power loader using a test specially developed for this case and based on a wet chemical process, or it is analyzed in a stationary x-ray fluorescence analysis device within 10 to 50 seconds after removal of the fine dust sample. In both of these methods of analysis the time required for the analysis is so short that before the driver of the power shovel dumps his load he can be informed which quality he happens to have on the shovel and in which shaft or on which heap it should be deposited.

A comparison of the process according to this invention with the presently used conventional method of sampling showed that the precision of the process of this invention in the phosphorus analysis is superior. Based on a series of experiments performed during the mining process it was proven that the error of the methods used (e.g., standard deviation) can be described as:

$$\delta(P) = 0.25 \sqrt{P}$$

for the conventional method, and $$\delta(P) = 0.14 \sqrt{P}$$

for the process according to this invention with P=phosphorus content of the bucket in percent by weight (100 percent=1).

Figure 5:
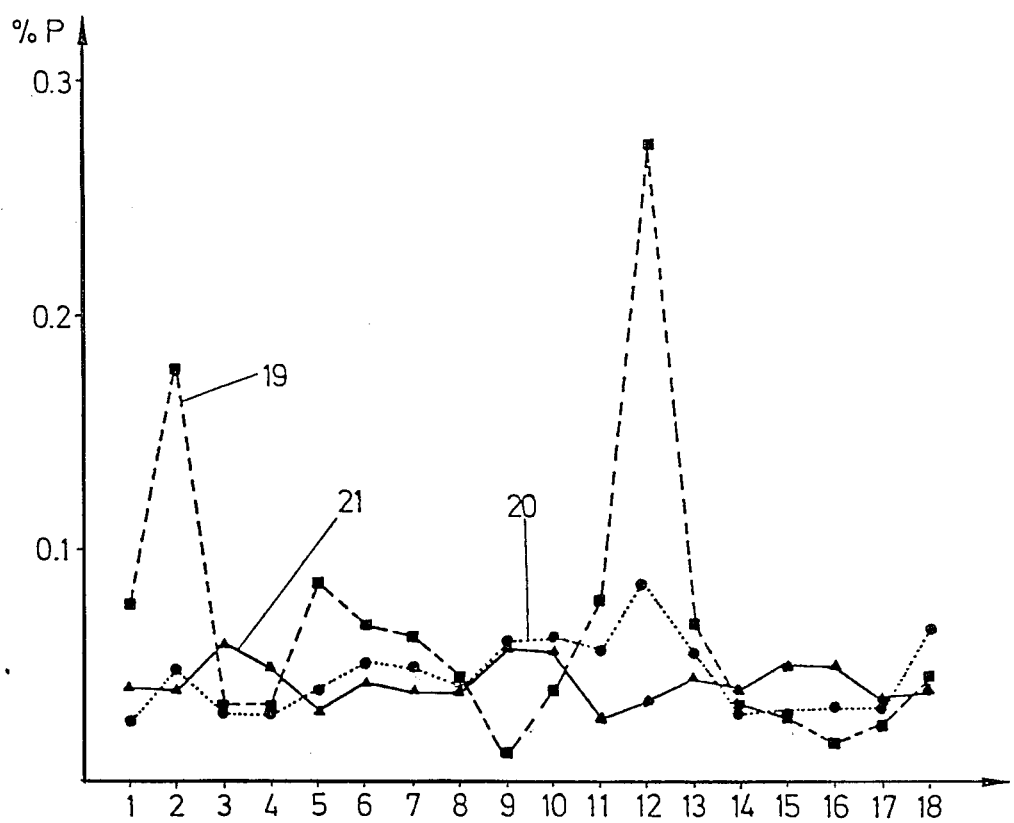
FIG. 5 is a diagram of the phosphorus content obtained by a conventional method compared to the content obtained by the process according to this invention.

FIG. 5 shows the average analytical values obtained from the shovel of the loader for both the conventional method (19) and the process according to this invention (20) compared with the analytical values of the corresponding car loads after emptying the shaft (21). In this series of the experiment every shovel was analyzed. During normal production, however, only the method of this invention is capable of analyzing each shovel because at most only 60 seconds are available for the analysis. Table I shows the impact of this invention method on the yield of the low phosphorus ore (0.08 percent phosphorus) in a certain mine area used as an example.

TABLE I

Yield of Ore with Low Phosphorus Content for Different Analytical Methods and Procedures

| | Percent of ore with low phosphorus content | Percent standard deviation of error of the method of analysis | |
|---|---|---|---|
| process according to this invention | 56.3 | 0.14 $\sqrt{P}$ | each bucket analyzed |
| conventional process | 50.9 | 0.25 $\sqrt{P}$ | |
| process according to this invention | 30 | 0.14 $\sqrt{P}$ | only every sixth bucket analyzed |
| conventional process | 20 | 0.25 $\sqrt{P}$ | |

The main advantages of the new process according to this invention, namely, speed and precision, clearly leads to a considerable increase in the production of low-phosphorus iron ore.

From the values obtained in the analysis of the individual shovels, it is also possible to calculate the analytic value for the total content of a single shaft or of the heaps.

The process according to this invention can be used in basically the same way for the analysis and subsequent sorting of other coarse to fine materials. Since the time elapsing between sampling and analysis is relatively short (about 1 min), this leaves time in most transport processes for the material to be conveyed to the store or container which is designated for that particular composition or quality.

We claim:

1. Process for sorting coarse to fine materials according to their chemical composition, in which samples are taken and analyzed, and in which the further dealing with the materials is controlled according to the results of the analysis, characterized in that the samples are taken in the form of an air swirled mixture of coarse dust and fine dust, and that the coarser dust is separated and at least a fraction of the fine dust is analyzed.

2. Process for sorting coarse to fine materials according to their chemical composition, in which samples are taken and analyzed, and in which the further dealing with said materials is controlled according to the results of the analysis, characterized in that the samples are taken in the form of an air swirled dust mixture of coarse dust and fine dust, the air swirled dust mixture being generated during movement of said material, that the coarser dust is separated from the fine dust, the fine dust having a grain size of less than 200 μm, and that at least a fraction of the fine dust is analyzed.

3. Process as claimed in claim 2 wherein in the sampling process the mixture of coarse dust and fine dust is produced by mechanical crushing.

4. Process as claimed in claim 2 or 3 wherein the coarser dust is removed from the mixture in one or more stages using a gravimetric method.

5. Process as claimed in claim 4 wherein dust particles of a specific composition are removed by magnetic separation.

6. Process as claimed in claim 5 wherein the fine dust is applied to a membrane filter and is passed on together with this filter for analysis.

7. Process as claimed in claim 6 wherein, for sampling, the mixture of coarse and fine dust is taken up and transmitted by suction.

8. Process as claimed in claim 4 wherein dust particles of a specific composition are removed by electrostatic separation.

9. Process as claimed in claim 8 wherein the fine dust is applied to a membrane filter and is passed on together with this filter for analysis.

10. Process as claimed in claim 9 wherein, for sampling, the mixture of coarse and fine dust is taken up and transmitted by suction.

11. Process as claimed in claim 2 or 3 wherein the coarser dust is removed from the mixture in one or more stages by filtering.

12. Process as claimed in claim 11 wherein dust particles of a specific composition are removed by magnetic separation.

13. Process as claimed in claim 12 wherein the fine dust is applied to a membrane filter and is passed on together with this filter for analysis.

14. Process as claimed in claim 13 wherein, for sampling, the mixture of coarse and fine dust is taken up and transmitted by suction.

15. Process as claimed in claim 11 wherein dust particles of a specific composition are removed by electrostatic separation.

16. Process as claimed in claim 15 wherein the fine dust is applied to a membrane filter and is passed on together with this filter for analysis.

17. Process as claimed in claim 16 wherein, for sampling, the mixture of coarse and fine dust is taken up and transmitted by suction.

18. Process as claimed in claim 2 wherein dust particles of a certain composition are removed by magnetic separation.

19. Process as claimed in claim 2 wherein the fine dust is applied to a diaphragm filter and is passed on together with this filter for analysis.

20. Process as claimed in claim 2 wherein, for sampling, the mixture of fairly coarse and fine dust is sucked up.

21. Process as claimed in claim 2 wherein the further dealing with the material is the transporting or further processing thereof.

22. Process as claimed in claim 2 wherein the mixture of coarse dust and fine dust is obtained as a by-product.

23. Process as claimed in claim 2 wherein the mixture of coarse dust and fine dust is produced artificially.

24. Process as claimed in claim 2 wherein dust particles of a certain composition are removed by electrostatic separation.

* * * * *

UNITED STATES PATENT AND TRADEMARK OFFICE
CERTIFICATE OF CORRECTION

PATENT NO. : 4,441,616

DATED : April 10, 1984

INVENTOR(S) : Rainer Konig, Hans-Ulrich Freund, Helga Heide, Rolf A. Sieglen

It is certified that error appears in the above-identified patent and that said Letters Patent is hereby corrected as shown below:

On the title page the assignee should read as follows:

-- [73] Luossavaara Kirrunavaara AB, Stockholm, Sweden --.

"Attorney, Agent, or Firm" should read -- Fisher, Christen & Sabol--.

Signed and Sealed this

Thirtieth Day of October 1984

[SEAL]

Attest:

GERALD J. MOSSINGHOFF

Attesting Officer

Commissioner of Patents and Trademarks